(12) United States Patent
Kahlman et al.

(10) Patent No.: US 9,063,092 B2
(45) Date of Patent: Jun. 23, 2015

(54) SENSING SYSTEM FOR SENSING A SUBSTANCE IN A FLUID

(75) Inventors: Josephus Arnoldus Hendrcus Maria Kahlman, Tiburg (NL); Theodorus Petrus Henricus Gerardus Jansen, Deurne (NL); Johannes Joseph Hubertina Barbara Schleipen, Eindhoven (NL)

(73) Assignee: Koninklijke Philips N.V., Eindhoven (NL)

(*) Notice: Subject to any disclaimer, the term of this patent is extended or adjusted under 35 U.S.C. 154(b) by 0 days.

(21) Appl. No.: 13/395,932

(22) PCT Filed: Sep. 13, 2010

(86) PCT No.: PCT/IB2010/054106
§ 371 (c)(1),
(2), (4) Date: Mar. 14, 2012

(87) PCT Pub. No.: WO2011/030318
PCT Pub. Date: Mar. 17, 2011

(65) Prior Publication Data
US 2012/0170042 A1    Jul. 5, 2012

(30) Foreign Application Priority Data
Sep. 14, 2009    (EP) .................................... 09170162

(51) Int. Cl.
*G01N 21/00*    (2006.01)
*G01N 21/84*    (2006.01)

(52) U.S. Cl.
CPC .................................. *G01N 21/8483* (2013.01)

(58) Field of Classification Search
CPC ............ G01N 21/774; G01N 21/7743; G01N 21/8483

USPC ........... 356/436, 445, 448, 243.1, 243.2, 300, 356/303, 306, 307, 319, 326, 244; 324/260; 422/82.11, 400; 436/164; 435/288.7
See application file for complete search history.

(56) References Cited

U.S. PATENT DOCUMENTS

| | | | |
|---|---|---|---|
| 4,529,308 A | 7/1985 | Rife | |
| 5,981,297 A * | 11/1999 | Baselt | ........................ 436/514 |

(Continued)

FOREIGN PATENT DOCUMENTS

| | | |
|---|---|---|
| WO | 2007029192 A1 | 3/2007 |
| WO | 2009007797 A1 | 1/2009 |

(Continued)

OTHER PUBLICATIONS

Han, S.J. et al "A Novel Zero-Drift Detection Method for Highly Sensitive GMR Biochips" IEEE Transactions on Magnetics, vol. 42, No. 10, Oct. 2006, pp. 3560-3562.

*Primary Examiner* — Tri T Ton
*Assistant Examiner* — Willie Merrell, II

(57) ABSTRACT

The invention relates to a sensing system for sensing a substance in a fluid. The sensing system comprises a sensing site (132) at which the substance is to be sensed and a reference site (131). A signal generation unit generates a sensing signal by sensing the sensing site (132) and a reference signal by sensing the reference site (131). The reference signal is used for normalizing the sensing signal, wherein the sensing site (132) and the reference site (131) are arranged such that a drift variation of the normalized sensing signal is within a noise variation of the normalized sensing signal. This improves the accuracy of the normalized sensing signal.

14 Claims, 10 Drawing Sheets

(56) References Cited

U.S. PATENT DOCUMENTS

| | | | |
|---|---|---|---|
| 6,429,022 B1* | 8/2002 | Kunz et al. | 436/164 |
| 7,604,984 B2* | 10/2009 | Frutos et al. | 435/288.7 |
| 7,627,201 B2* | 12/2009 | Tiefenthaler | 385/12 |
| 2004/0058385 A1* | 3/2004 | Abel et al. | 435/7.1 |
| 2008/0218165 A1* | 9/2008 | Kahlman et al. | 324/260 |
| 2010/0144052 A1* | 6/2010 | Pi | 436/164 |

FOREIGN PATENT DOCUMENTS

| | | |
|---|---|---|
| WO | 2009039437 A1 | 3/2009 |
| WO | 2009098623 A1 | 8/2009 |

\* cited by examiner

SENSING SYSTEM FOR SENSING A SUBSTANCE IN A FLUID

FIELD OF THE INVENTION

The invention relates to a sensing system for sensing a substance in a fluid, a sensing device for cooperating with an analyzing device for sensing a substance in a fluid, the analyzing device, a sensing method for sensing a substance in a fluid, and a computer program for sensing a substance in a fluid.

BACKGROUND OF THE INVENTION

A magneto-optical biosensor for detecting magnetic beads at several binding spots on an optical interface using frustrated total internal reflection (FTIR) can be used as a sensing system for sensing a substance in a fluid. For performing FTIR light from a light source is directed onto the optical interface such that an evanescent field is generated at the binding spots. The magnetic beads at the binding spots influence the evanescent field, wherein this influence is detected as intensity variations in the light reflected from the optical interface. The detected intensity variations are used for determining the concentration of the magnetic beads at the binding spots. By binding or non-binding of these magnetic beads to the optical interface in a biological assay, the presence of various substances, e.g. drugs-of-abuse or cardiac troponin-I, are detected in real matrices like saliva or blood by detecting the magnetic beads, which have attached the substances, within the evanescent field. One dedicated area on the biosensor optical interface is modified such that magnetic beads cannot reach the evanescent field and the total internal reflection is not frustrated, thereby keeping the detected signal at its maximum, i.e. reference, level. This so-called True-White-Reference (TWR) is used to suppress by normalization common-mode intensity-variations in each of the binding spots induced by, for example, the light source.

SUMMARY OF THE INVENTION

It is an object of the present invention to provide a sensing system for sensing a substance in a fluid, wherein the suppression of fluctuations of a sensing signal, which are not induced by fluctuations of a substance to be sensed, is improved.

In a first aspect of the present invention a sensing system for sensing a substance in a fluid is provided, wherein the sensing system comprises:
a sensing site at which the substance is to be sensed,
a reference site,
a signal generation unit for generating a sensing signal by sensing the sensing site and for generating a reference signal by sensing the reference site,
a normalization unit for generating a normalized sensing signal by normalizing the sensing signal using the reference signal,
wherein the reference site and the signal generation unit are adapted such that the reference signal is not influenced by the substance and the fluid, and the sensing site and the signal generation unit are adapted such that the sensing signal is dependent on the substance at the sensing site,
wherein the sensing site and the reference site are arranged such that a drift variation of the normalized sensing signal is within a noise variation of the normalized sensing signal.

The invention is based on the recognition that the sensing signal is not only influenced by common-mode intensity-variations at the sensing site and at the reference site, but also by intensity-variations which are spatially varying, i.e. it has been observed that fluctuations of the sensing signal and fluctuations of the reference signal are spatially non-uniform. These spatially non-uniform sensing fluctuations adversely affect the sensing signal and can generally not be eliminated by the above described normalization of the prior art. The invention is based on the recognition that the influence of the spatially non-uniform fluctuations of the signal can be reduced by modifying the arrangement of the sensing site and the reference site. The reference site and the sensing site can be arranged such that this reduction of the influence of the spatially non-uniform fluctuations is such that the drift variation of the normalized sensing signal is within a noise variation of the normalized sensing signal, i.e. preferentially such that the drift variations of the normalized sensing signal are smaller than the noise variations of the normalized sensing signal.

Variations of the sensing signal can be common-mode variations, i.e. variations being spatially uniform, and spatially non-uniform variations. The common-mode variations can be suppressed by normalizing the sensing signal with a TWR signal of a single TWR as described in the prior art. The remaining spatially non-uniform variations can be regarded as comprising drift variations, wherein a drift variation is a comparatively long-term change of the sensing signal, and noise variations of the sensing signal, which describe a comparatively short-term change. The drift and noise variations of a sensing system can easily be determined by a person skilled in the art. The noise variations can be regarded as the variance of the sensing signal in the comparatively short-term. Preferentially, the expression "comparatively long-term" with respect to drift relates to some minutes, for example, at least two minutes, at least three minutes or at least five minutes, and the expression "comparatively short-term" with respect to noise relates to some seconds, for example, less than 30 seconds, less than 20 seconds or less than 10 seconds.

The signal generation unit is preferentially adapted to generate a sensing signal by using FTIR. Preferentially, at the sensing site a binding element is present for binding the substance. The sensing system preferentially comprises magnetic beads which can attach the substance in the fluid and which can be attracted to the sensing site by magnetic forces. The substance with the attached magnetic beads binds to the sensing site and the magnetic beads, which are bound in this way via the substance to the sensing site, are detected by the signal generation unit using FTIR. Thus, the corresponding sensing signal depends preferentially on the concentration of the bound substance, i.e. the bound magnetic beads, at the sensing site. The reference signal is not influenced by the fluid, the substance or the magnetic beads.

The sensing system can comprise one or several sensing sites and one or several reference sites.

The drift and noise variations relate to fluctuations of the normalized sensing signal in a situation in which the amount of the substance and the fluid at the sensing site is not modified. In this situation the variations of the sensing signal are not caused by, for example, temporally varying concentrations of the substance at the sensing site.

In a preferred embodiment, the distance between the sensing site and the reference site is chosen such that the drift variation of the normalized sensing signal is within the noise variation of the normalized sensing signal.

The fluctuations are preferentially temporal fluctuations, i.e. the sensing signal and the reference signal are measured over time.

It is preferred that a distance between the sensing site and the reference site is smaller than 100 µm. If this distance is smaller than 100 µm, the fluctuations of the sensing signal are further decreased.

It is further preferred that the sensing system comprises several sensing sites and several reference sites, wherein the sensing system is adapted to be operated in a calibration mode and in a measurement mode, wherein the sensing system comprises a determination unit for determining in the calibration mode for a sensing site of the several sensing sites at least one reference site of the several references sites for normalizing such that a drift variation of the normalized sensing signal of the sensing site of the several sensing sites is within a noise variation of the normalized sensing signal of the sensing site of the several sensing sites, wherein the sensing system is adapted to normalize, in the measurement mode, the sensing signal of the sensing site of the several sensing sites by the at least one reference signal of the at least one reference site determined by the determination unit. This allows adapting the normalization process to the actually present spatially non-uniform fluctuations, thereby further decreasing the influence of the spatially non-uniform fluctuations on the normalized sensing signal.

In a further embodiment, it is not distinguished between a calibration mode and a measurement mode. Reference signals and sensor signals are being retrieved at the same time, for example, in the same CCD frame, and based on the retrieved reference and sensor signals for each sensing site of several sensing sites at least one reference site of the several reference sites is determined for normalizing such that a drift variation of the normalized sensing signal of the sensing site of the several sensing sites is within a noise variation of the normalized sensing signal of the sensing site of the several sensing sites. For this determination of the at least one reference site, which is used for normalizing the respective sensing signal, the normalized sensing signal is determined, which can be provided to a user.

In an embodiment, the several sensing sites and several reference sites are spatially non-uniformly arranged. In addition or alternatively, the several sensing sites and several reference sites have non-uniform dimensions.

It is preferred that the sensing system comprises several sensing sites and several reference sites which are arranged in an interleaved manner. The sensing sites and the reference sites form preferentially a checkerboard pattern.

It is further preferred that the sensing sites and the reference sites are arranged such that the sensing site has reference sites as nearest neighbors in at least two directions.

This allows to suppress spatially non-uniform fluctuations of the sensing signal, which are not caused by a spatially non-uniform distribution of the substance at the sensing sites, in two spatial directions. The two directions are preferably orthogonal to each other.

It is further preferred that the sensing site and the reference site are integrated. This decreases the distance between the sensing site and the reference site and, thus, decreases the spatially non-uniform fluctuations of the sensing signal which are not generated by a spatially non-uniform distribution of the substance at the sensing sites. The integrated sensing site and reference site can be formed as an inner sensing region within an outer reference region or as an inner reference region with an outer sensing region. In an embodiment, a circular sensing region comprises radial reference regions.

It is further preferred that the sensing system comprises several sensing sites and several reference sites, wherein the sensing sites and the reference sites are arranged in alternating parallel lines. Preferentially, the alternating parallel lines extend in a deformation direction in which the sensing system is more deformable than in another direction. This allows reducing spatially non-uniform fluctuations of the sensing signal, which are not caused by a spatially non-uniform distribution of the substance at the sensing sites, at least in a direction, in which these non-spatial fluctuations are more pronounced than in another direction. In particular, the alternating parallel lines extend in a deformation direction in which the sensing system has the strongest deformations.

In an embodiment, the sensing system comprises several sensing sites aligned in a deformation direction in which the sensing system is more deformable than in another direction. This allows correcting the sensing signal for spatially non-uniform deformations in a direction in which the deformations are stronger than in another direction.

The deformations preferentially refer to deformations of a sensing surface of the sensing system on which the reference sites and the sensing sites are arranged.

It is further preferred that the sensing system comprises several sensing sites arranged in parallel lines, wherein between two parallel lines the reference site is located, wherein the reference site has an elongated shape with a longitudinal and a transversal dimension, wherein the longitudinal dimension is parallel to the parallel lines of the sensing sites. Preferentially, the length of the longitudinal dimension of the reference site is substantially equal to the length of the parallel lines of the sensing sites.

Preferentially, the longitudinal dimension extends in a deformation direction in which the sensing system is more deformable than in another direction. Also this ensures that spatially non-uniform fluctuations of the sensing signal, which are not caused by a spatially non-uniform distribution of the substance at the sensing sites, are strongly reduced.

It is further preferred that the sensing system comprises several reference sites forming a grid with several grid elements and several sensing sites, wherein the sensing sites are arranged within the several grid elements. A grid element is preferentially a mesh of the grid, wherein the sensing sites are located within the meshes of the grid formed by the reference sites. This allows reducing spatially non-uniform fluctuations of the sensing signal, which are not caused by spatially non-uniform distribution of the substance on the sensing sites, if these fluctuations are caused by deformations of the sensing system in different directions.

The normalization unit is preferentially adapted to combine several reference signals corresponding to the several reference sites and to normalize the sensing signal by using the combined reference signal.

The combination is preferentially performed by determining the reference sites being the nearest neighbors of the sensing site and by weightily averaging the reference signals of the determined reference sites for generating a combined reference signal. In an embodiment, the weights for the determined reference signals corresponding to the reference sites being nearest neighbors are equal. In another embodiment, the weight for a reference signal depends on the inverse of the reference signal at a certain time.

The sensing system preferentially comprises a sensing device including the sensing site and the reference site and an analyzing device including the signal generation unit and the normalization unit. The sensing device is preferentially a cartridge for receiving a fluid like blood, saliva or urine, for filtering the fluid and for transferring the filtered fluid to the sensing site of the cartridge. The cartridge is preferentially disposable and is adapted for single use only. The analyzing device is preferentially adapted to be used several times with different sensing devices. Thus, in an embodiment a fluid like blood, saliva or urine is put on a filter of a sensing device, the fluid is filtered and the filtered fluid is transferred to a sensing region in which the sensing site is present. The sensing device is arranged in the analyzing device and a substance within the fluid in the sensing region, in particular, at the sensing site, is analyzed by the analyzing device. After the sensing device has been used, it is preferentially discarded, whereas the analyzing device is used for a next analyzing procedure.

It is further preferred that the sensing system comprises a sensing device including the sensing site and the reference site and an analyzing device including the signal generation unit and the normalization unit, wherein the analyzing device further comprises an aligning unit for detecting the position of the reference site of the sensing device and for aligning the sensing device and the analyzing device with respect to each other by using the detected position of the reference site. This allows aligning the sensing device with respect to the analyzing device without needing or with less additional markers.

In a further aspect of the present invention a sensing device for cooperating with an analyzing device for sensing a substance in a fluid is presented, wherein the sensing device comprises:
  a sensing site at which the substance is to be sensed,
  a reference site,
  wherein the analyzing device comprises:
  a signal generation unit for generating a sensing signal by sensing the sensing site and for generating a reference signal by sensing the reference site,
  a normalization unit for generating a normalized sensing signal by normalizing the sensing signal using the reference signal,
  wherein the reference site and the signal generation unit are adapted such that the reference signal is not influenced by the substance and the fluid, and the sensing site and the signal generation unit are adapted such that the sensing signal is dependent on the substance at the sensing site,
  wherein the sensing site and the reference site are arranged such that a drift variation of the normalized sensing signal is within a noise variation of the normalized sensing signal.

In a further aspect of the present invention an analyzing device for cooperating with a sensing device for sensing a substance in a fluid is presented, wherein the sensing device comprises:
  a sensing site at which the substance is to be sensed,
  a reference site,
  wherein the analyzing device comprises:
  a signal generation unit for generating a sensing signal by sensing the sensing site and for generating a reference signal by sensing the reference site,
  a normalization unit for generating a normalized sensing signal by normalizing the sensing signal using the reference signal,
  wherein the reference site and the signal generation unit are adapted such that the reference signal is not influenced by the substance and the fluid, and the sensing site and the signal generation unit are adapted such that the sensing signal is dependent on the substance at the sensing site,
  wherein the sensing site and the reference site are arranged such that a drift variation of the normalized sensing signal is within a noise variation of the normalized sensing signal.

In a further aspect of the present invention a sensing method for sensing a substance in a fluid is presented, wherein the sensing method comprises the steps of:
  generating a sensing signal by sensing the substance at a sensing site,
  generating a reference signal by sensing a reference site,
  generating a normalized sensing signal by normalizing the sensing signal using the reference signal,
  wherein the reference site and the signal generation unit are adapted such that the reference signal is not influenced by the substance and the fluid and the sensing site and the signal generation unit are adapted such that the sensing signal is dependent on the substance at the sensing site,
  wherein the sensing site and the reference site are arranged such that a drift variation of the normalized sensing signal is within a noise variation of the normalized sensing signal.

It shall be understood that a preferred embodiment of the invention can also be any combination of the dependent claims with the respective independent claim.

These and other aspects of the invention will be apparent from and elucidated with reference to the embodiments described herein after.

DETAILED DESCRIPTION OF EMBODIMENTS

Figure 1:
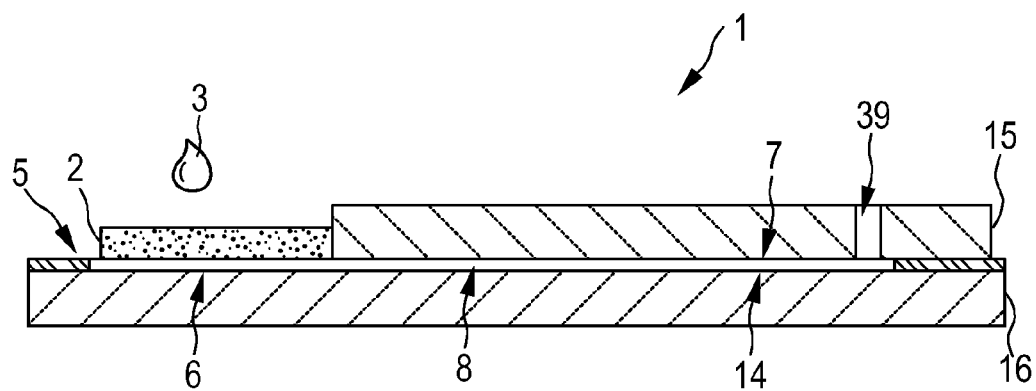
FIG. 1 shows schematically and exemplarily a cross-section of a sensing device.

FIG. 1 shows schematically and exemplarily a sensing device 1 for sensing a substance in a fluid 3. The sensing device 1 comprises a filter element 2 for filtering the fluid 3 and a capillary structure 5 for generating capillary forces. The capillary structure 5 is attached to the filter element 2 by using preferentially an adhesive. The capillary structure 5 is, in this embodiment, made of a double-sided tape which is adhesive on two sides.

The sensing device 1 comprises a filtering location 6 at which the filter 2 is located and a sensing location 7 at which a substance within the fluid 3 is detectable, wherein the capillary structure 5 is formed such that the filtered fluid 3 is guided from the filtering location 6 to the sensing location 7 by capillary forces.

Figure 2:
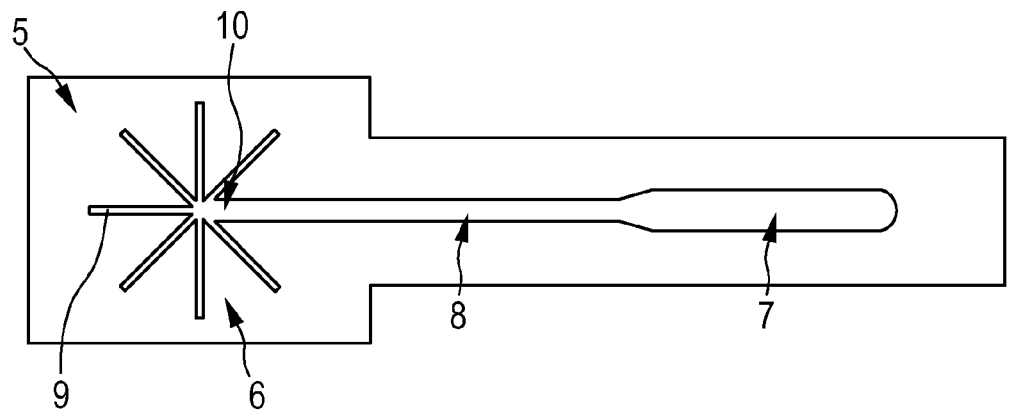
FIG. 2 shows schematically and exemplarily a capillary structure of the sensing device.
Figure 3:
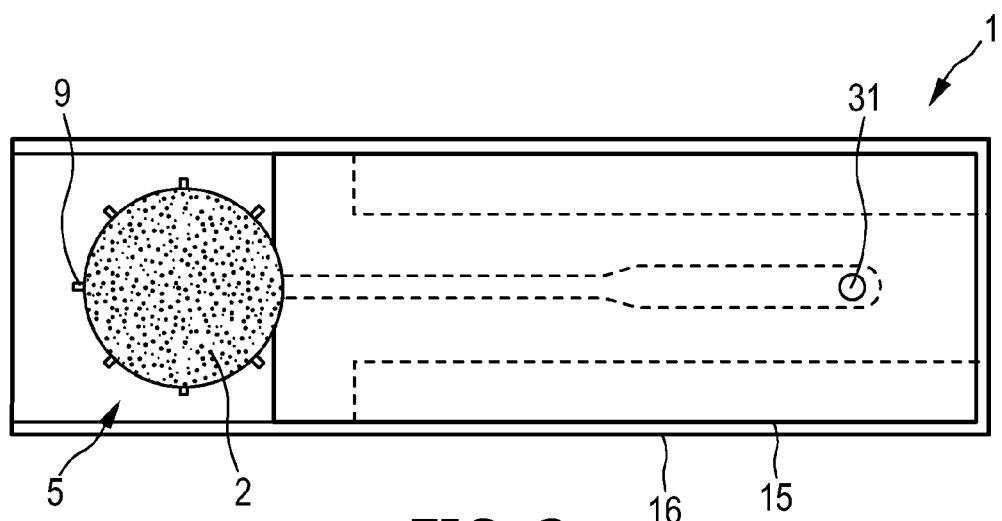
FIG. 3 shows schematically and exemplarily a top view on the sensing device.

The capillary structure 5 comprises a collecting channel, which connects the filtering location 6 with the detection location 7, and guiding channels 9 located at the filtering location 6, wherein the guiding channels 9 extend from an end of the connected channel 8. In this embodiment the guiding channels 9 extend radially from the end 10 of the connecting channel 8. The capillary structure 5 is schematically and exemplarily shown in more detail in FIG. 2. FIG. 3 shows schematically and exemplarily a top view on the sensing device 1 which is shown in a sectional view in FIG. 1.

The sensing device 1 comprises a sensing cavity 14 which is located at the sensing location 7 and in which a substance of the fluid 3 is detectable. This sensing cavity 14 is formed by a first part 15 and a second part 16 of the sensing device 1 together with the capillary structure 5. In addition, the first part 15 and the second part 16 form together with the capillary structure 5 the connecting channel 8. The first part 15 and the second part 16 are preferentially attached to each other via an adhesive, in particular, via the double-sided tape forming the capillary structure 5. The first part 15 and the second part 16 are plastics substrates which are injection molded and preferentially transparent to visible light. The first part 15 can be regarded as an upper substrate or a closing element or cover element and the second part 16 can be regarded as a lower substrate or a base element of the sensing device 1. The first part 15 comprises a vent 39 for allowing a gas to leave the capillary structure 5.

In this embodiment, the filter element 2 is a blood separation filter and the sensing device 1 forms a cartridge which is preferentially disposable. The sensing device 1 is preferentially used in point-of-care diagnostics. The sensing device 1 is preferentially adapted for detecting a low concentration bio marker in a sample of whole blood, in particular, in a finger prick sample of, for example, 25 μl. The sensing location 7 preferentially comprises an immuno assay.

Figure 4:
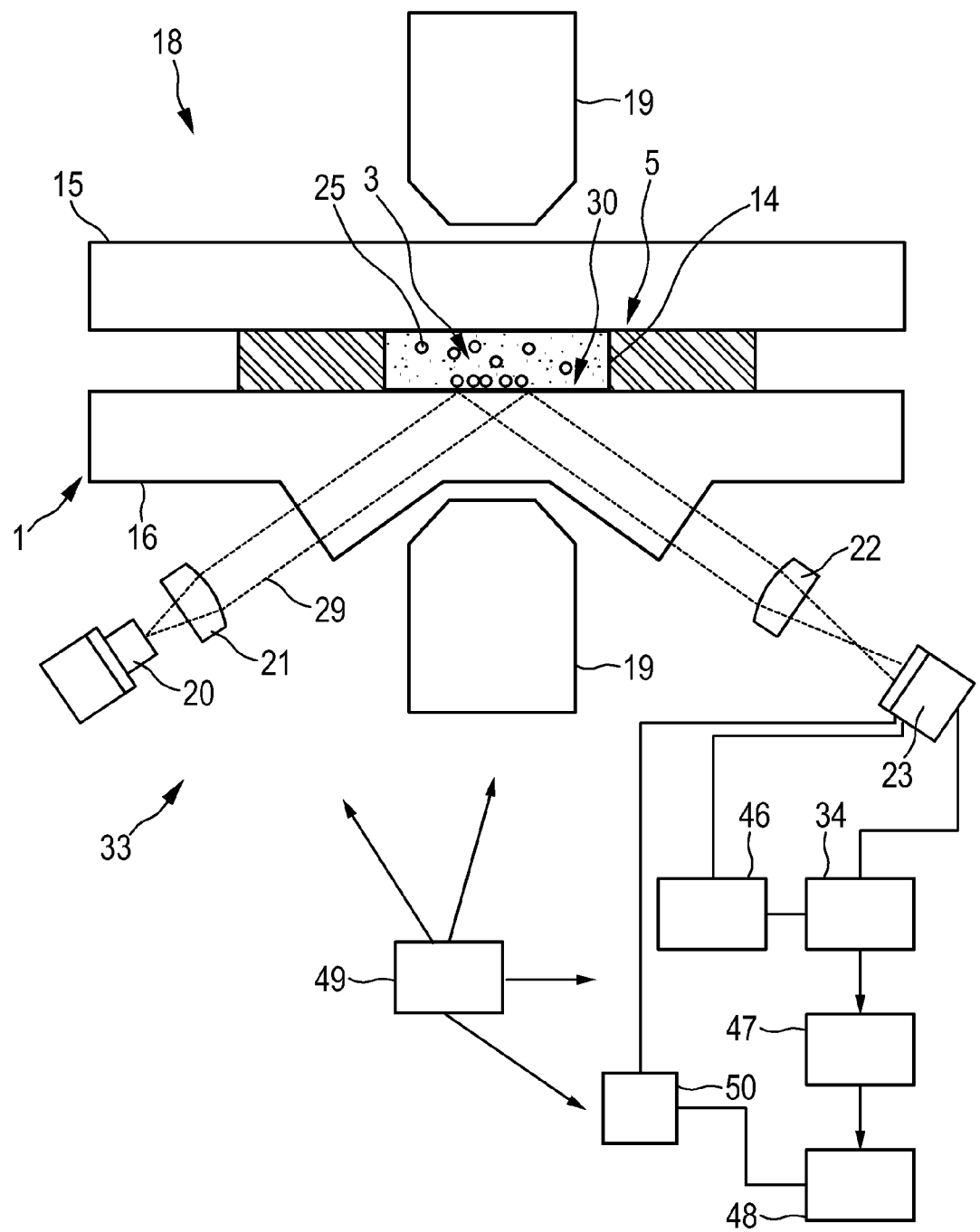
FIG. 4 shows schematically and exemplarily the sensing device introduced into an analyzing device.

FIG. 4 shows schematically and exemplarily an analyzing device 18 for cooperating with the sensing device 1 for sensing a substance in the fluid 3. The analyzing device 18 is adapted for determining a substance in the fluid 3 which is located in the sensing cavity 14 of the sensing device 1. The analyzing device 18 comprises, in this embodiment, a magnetic element 19 which provides a magnetic field for forcing magnetic beads within the sensing cavity 14 onto a sensing surface 30 of the second part 16 of the sensing device 1. The magnetic beads 25 on the sensing surface 30 are detected by, in this embodiment, illuminating the sensing surface 30 with a light beam 29 generated by a light source 20 which is, for example, a laser device or a light emitting diode and by detecting the light reflected from the sensing surface 30 by a detector 23. The detector 23 is, for example, a photodetector or a two-dimensional camera. Optical elements 21 and 22 can be arranged in the light beam 29 for generating parallel light or focusing the light beam 29, respectively. The optical elements 21, 22 are preferentially lenses. The optical element 22 is preferentially being used for imaging the sensing surface 30 onto the detector surface 23, wherein the focus is preferentially slightly in front of the detector surface.

The configuration sketched in FIG. 4 shows a detection of changes at the sensing surface using the FTIR method (frustrated total internal reflection). If a beam of light reflects on the interface between a medium with a higher refractive index, for example the second part 16, and a lower refractive index, for example the fluid, there is a certain critical angle of incidence above which there is a situation of total internal reflection (TIR). The shown detection configuration (regarding refractive indices and angle of incidence) is such that there is total internal reflection of the incoming beam. Although the light is totally reflected in such a situation, there is still penetration of the light in a very thin layer of the medium with the low refractive index. This is called an evanescent field, the intensity of which decays exponentially in the low refractive index medium with a characteristic penetration depth of the order of the wavelength of the light. So, in practice the penetration depth is preferentially less than 0.5 micrometer. If magnetic beads 25 are bound at a sensing site to the sensing surface 30, the optical properties of this very thin first fluid layer of preferentially about 0.5 micrometer are changed leading to a reduction of the intensity of the reflected light beam. This is caused by absorption and scattering of the evanescent light (FTIR; frustrated total internal reflection). As a result the signal of the detector 23 changes.

Figure 5:
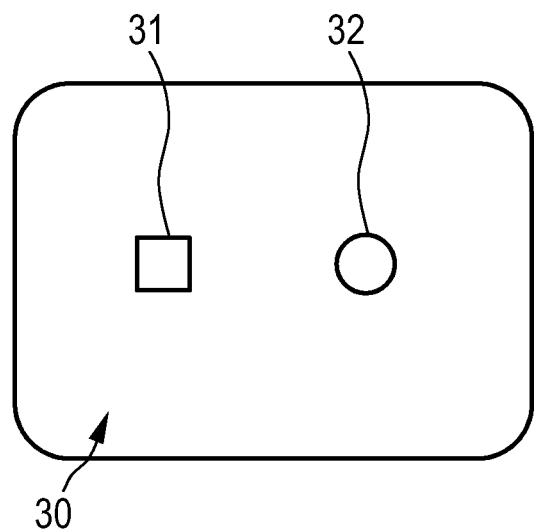
FIG. 5 shows schematically and exemplarily a sensing surface of the sensing device comprising a reference site and a sensing site.

The light source 20, the optional optical elements 21 and 22, and the detector 23 form a signal generation unit 33 for generating a sensing signal by sensing a sensing site and for generating a reference signal by sensing a reference site. A sensing site 32 and a reference site 31 on the sensing surface 30 are schematically and exemplarily shown in FIG. 5.

The light source 20 is adapted to illuminate the sensing site 32 and the reference site 31 of the sensing surface 30 and to detect the light reflected at the sensing site 32 and the reference site 31 for generating a sensing signal depending on the light reflected at the sensing site 32 and a reference signal depending on the light reflected at the reference site 31.

The reference site 31 is adapted such that the reference signal is not influenced by the substance and the fluid in the sensing cavity 14, whereas the sensing signal is dependent on the substance, i.e. on the magnetic beads which have attached the substance, at the sensing site 32.

In order to ensure that the reference signal is not influenced by the substance and the fluid, the reference site 31 is preferentially covered by a material having a height with respect to the sensing surface 30 being substantially larger than the penetration depth of the evanescent field and having a refractive index ensuring total reflection at the reference site 31, i.e. in this embodiment, having a refractive index $n_{ref}$ such that the entrance angle of the incoming sensing beam 29 is larger than $\sin^{-1}(n_{ref}/n_{cartridge})$, where this entrance angle of the incoming sensing beam 29 has been chosen such that this entrance angle is larger than $\sin^{-1}(n_{fluid}/n_{cartridge})$, with $n_{fluid}$ being the refractive index of the fluid to be analyzed and $n_{cartridge}$ being the refractive index of the sensing surface material. The reference site 31 is preferentially covered by a material having a height with respect to the sensing surface being preferentially at least five times larger than the penetration depth of the evanescent field.

Referring again to FIG. 4, the analyzing device further comprises a normalization unit 34 for generating a normalized sensing signal by normalizing the sensing signal using the reference signal.

The reference site 31 and the sensing site 32 are arranged on the sensing surface 30 such that a drift variation of the normalized sensing signal is within a noise variation of the normalized sensing signal. The drift and noise variations relate to fluctuations of the normalized sensing signal in a situation in which the amount of the substance, of the fluid or of another element at the sensing site 32 is not modified. In this situation the fluctuations of the sensing signal are not caused by, for example, temporally varying concentrations of the substance at the sensing site 32.

The reference site 31 and the sensing site 32 have a distance relative to each other such that a drift variation of the normalized sensing signal is within a noise variation of the normalized sensing signal. This distance is preferentially smaller than 100 µm, further preferred smaller than 50 µm and even further preferred smaller than 10 µm.

Figure 6:
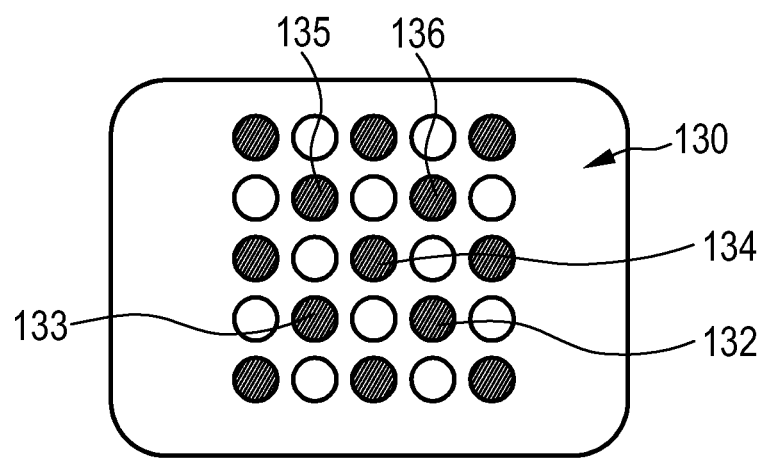
FIG. 6 shows a further embodiment of the sensing surface of the sensing device.

FIG. 6 shows schematically and exemplarily a further embodiment of a sensing surface 130 of a sensing device. Also this sensing surface 130 can be used together with the above described sensing device 1 and analyzing device 18.

The sensing surface 130 comprises several sensing sites indicated by shaded circles and several reference sites indicated by blank circles which are arranged in an interleaved pattern. The sensing sites and the reference sites form a checkerboard pattern. In this embodiment, a sensing site has several reference sites as nearest neighbors in at least two directions being orthogonal to each other, and the normalization unit is preferentially adapted to weightedly combine the reference signals of the reference sites being the nearest neighbors and to use the combined reference signal for normalizing the sensing signal of the respective sensing site.

Figure 7:
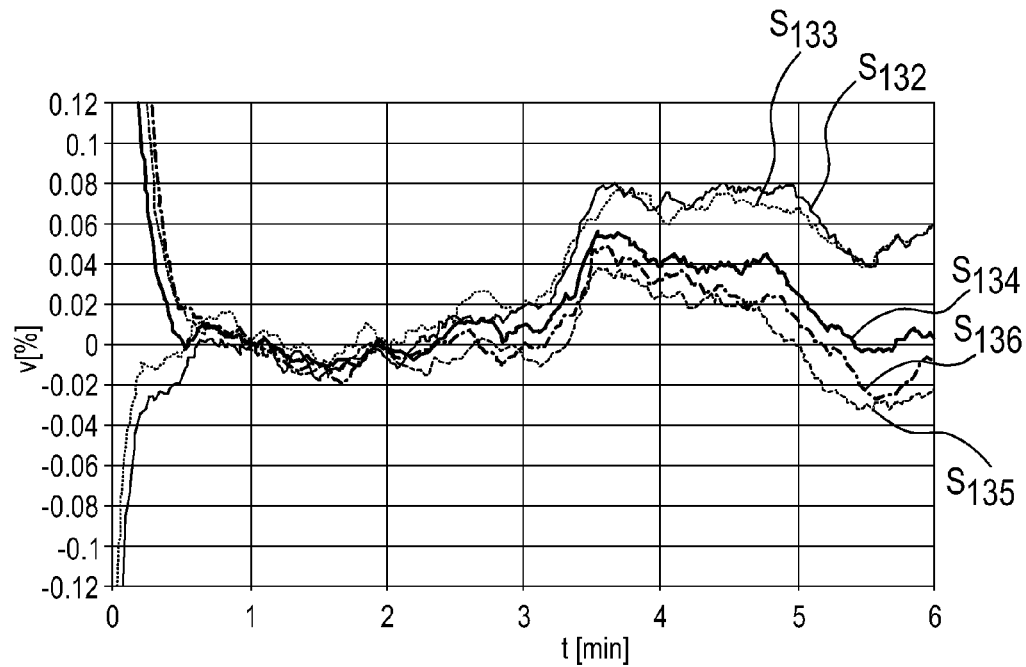
FIG. 7 shows schematically and exemplarily variations of different sensing signals.

FIG. 7 shows schematically and exemplarily variations of sensing signals $S_{132}, S_{133}, S_{134}, S_{135}, S_{136}$ with respect to the respective sensing signal at the time t=1 min in percent. The sensing signals $S_{132}, S_{133}, S_{134}, S_{135}, S_{136}$ correspond to the sensing sites 132 . . . 136.

Figure 8:
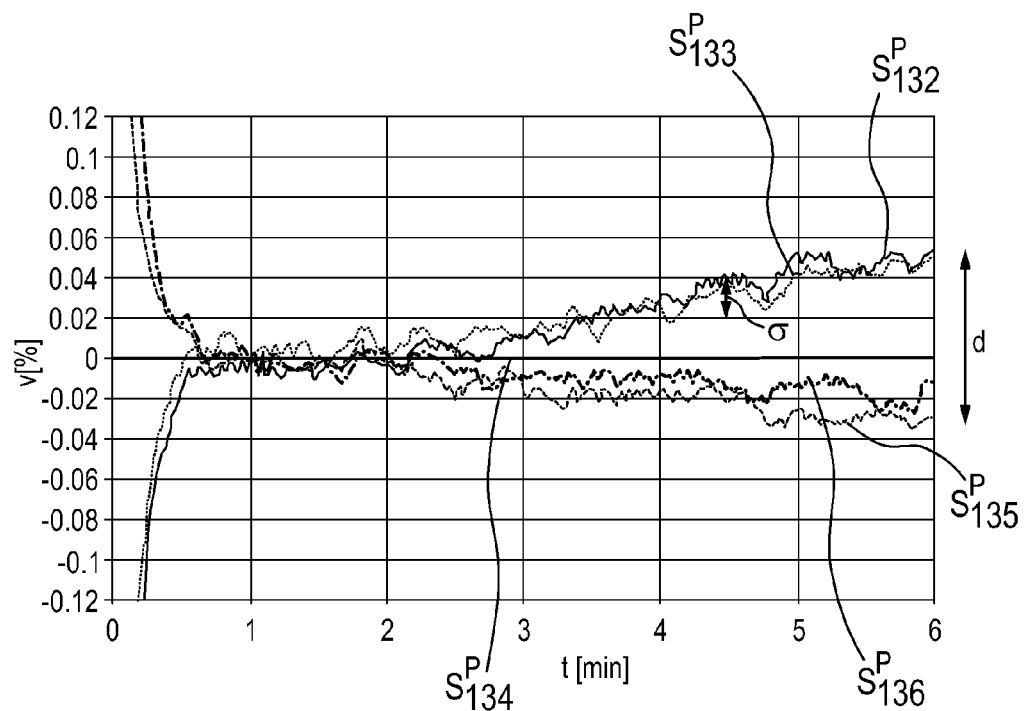
FIG. 8 shows schematically and exemplarily variations of different sensing signals being normalized in accordance with the prior art.

FIG. 8 schematically and exemplarily illustrates a normalization of the sensing signals performed in the prior art. In order to illustrate this normalization, the sensing signal of the sensing site 134 is regarded as a reference signal, and the sensing signals of the sensing sites 132 . . . 136 are normalized by the sensing signal of the sensing site 134. Such a prior art normalization allows to reduce fluctuations of the sensing signals being common-mode variations. Spatially non-uniform fluctuations are still present. As it can be seen in FIG. 8, the variations of the normalized sensing signals $S^P_{132}, S^P_{133}, S^P_{135}, S^P_{136}$ include noise variations indicated schematically and exemplarily for the normalized sensing signal $S^P_{133}$ by $\sigma$ and drift variations indicated in FIG. 8 schematically and exemplarily by d.

Thus, the drift variation d of the normalized sensing signal is not within the noise variation $\sigma$ of the normalized sensing signal. This comparison of the drift variation and of the noise variation can of course only be performed after waiting a comparable long-time being sufficient to show the drift. This time is preferentially in the range of some minutes, for example, at least two minutes, at least three minutes or at least five minutes. Thus, preferentially drift variations observed during a time span of at least two minutes, further preferred of at least three minutes, and even further preferred of at least five minutes, are compared with the noise variance.

Also in FIG. 8 the variations are variations with respect to the respective normalized sensing signal at the time t=1 min in percent.

In this embodiment, reference sites being the nearest neighbors of a sensing site are determined, the reference signals of the determined reference sites are averaged for generating a combined reference signal, and the combined reference signal is used for normalizing the sensing signal of the respective sensing site. The normalization of a sensing signal S(t) can be described by following equation:

$$S^n(t) = \frac{\frac{S(t)}{S(t_0)}}{\frac{1}{N}\sum_{i=1}^{N}\frac{R_i(t)}{R_i(t_0)}}, \quad (1)$$

wherein $S^n(t)$ indicates the normalized sensing signal, $t_0$ defines a reference time, N is the number of the determined nearest neighbors of reference sites, and $R_i(t)$ indicates a reference signal of the i-th nearest neighbor being a reference site.

Figure 9:
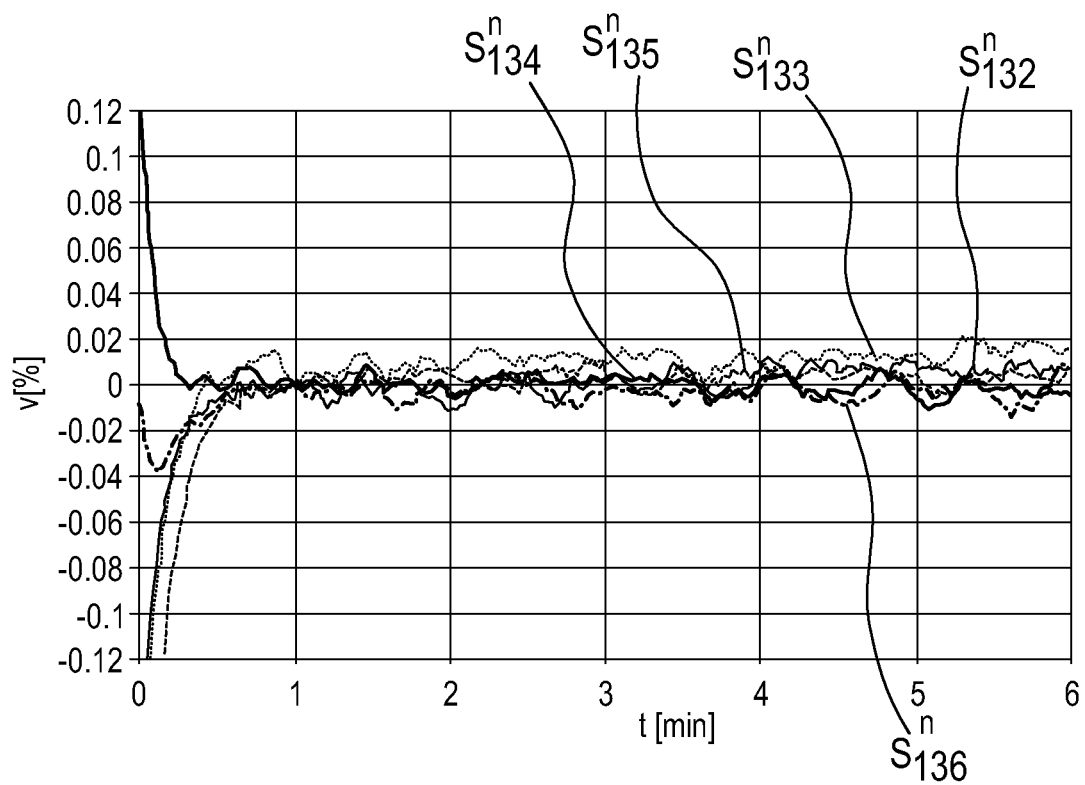
FIG. 9 shows schematically and exemplarily variations of different sensing signals being normalized in accordance with the invention.

FIG. 9 shows schematically and exemplarily variations of sensing signals $S^n_{132}, S^n_{133}, S^n_{134}, S^n_{135}, S^n_{136}$ which have been normalized in accordance with equation (1). As it can be seen in FIG. 9, a drift variance of the normalized sensing signal is not present even after a comparable long term of five minutes after $t_0$=1 min. The noise variations can still be seen. Thus, the normalization is performed such that the drift variation of the normalized sensing signal is within the noise variation of the normalized sensing signal.

Also in FIG. 9 the variations are variations with respect to the respective normalized sensing signal at the time t=1 min in percent.

In equation (1) the division by the sensing signal and reference signal, respectively, at a certain time $t_0$ can be omitted.

The normalization suppresses influences of deformations of the sensing surface 130 on the sensing signals in both directions, the horizontal as well the vertical direction in FIG. 6. Preferentially, this normalization allows reducing the fluctuations of the sensing signal to below 0.02% of the measured sensing signal.

Figure 10:
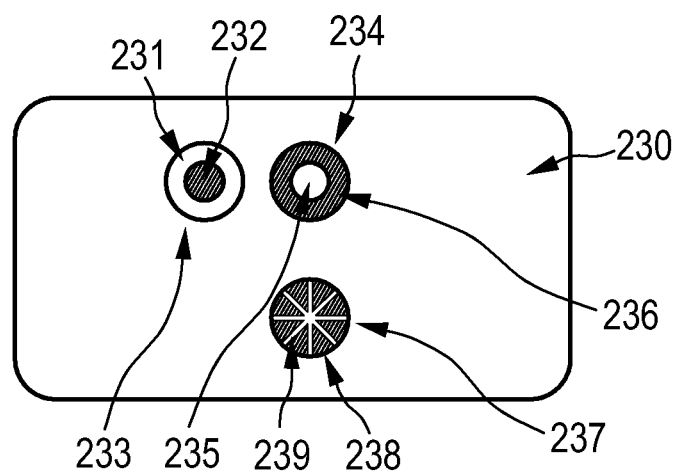
FIGS. 10 to 13 show further embodiments of the sensing surface of the sensing device.

FIG. 10 shows schematically and exemplarily a further sensing surface 230 comprising integrated combinations 233, 234, 237 of a reference site and a sensing site. The combined sensing and reference site 233 comprises an inner sensing region 232 with an outer reference region 231. The combined sensing and reference site 234 comprises an inner reference region 235 and an outer sensing region 236, and the combined sensing and reference site 237 comprises a circular sensing region 238 with radial reference region 239. In the combined reference and sensing sites 233, 234 and 237 preferentially the sensing regions, i.e. the biological capture probes comprising these sensing regions, are printed on top of the respective reference region.

If the sensing device comprises the sensing surface 230 schematically and exemplarily shown in FIG. 10 the normalization unit 34 is adapted to use the reference signal of a reference region of a combined sensing and reference site for normalizing the sensing signal of the sensing region of the same combined sensing and reference site.

Figure 11:
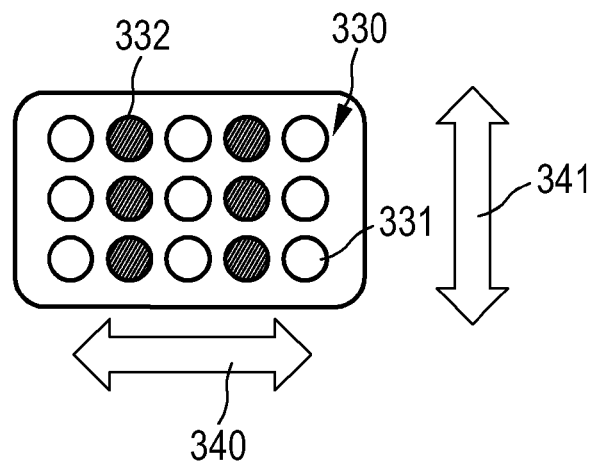

FIG. 11 shows schematically and exemplarily a further embodiment of a sensing surface 330 which can be the sensing surface of the above described sensing device and which can be used with the above described analyzing device.

The sensing surface 330 comprises several sensing sites 332 and several reference sites 331, wherein the sensing sites 332 and the reference sites 331 are arranged in alternating parallel lines. The alternating parallel lines extend in a deformation direction 341 in which the sensing surface 333 is more deformable than in another direction 340. In this embodiment, the deformations of the sensing surface 330 are strongest in the direction 341 and weakest in the direction 340.

Preferentially, for normalizing a sensing signal of a sensing site 332 the two nearest reference sites, i.e. the corresponding reference signals, in a horizontal line in FIG. 11 are combined for normalizing the respective sensing signal. The combination is preferentially an averaging of the reference signals of the two nearest neighbors of the respective sensing site, i.e. of the two nearest reference sites to the respective sensing site. Also this normalization can be performed in accordance with equation (1).

Figure 12:
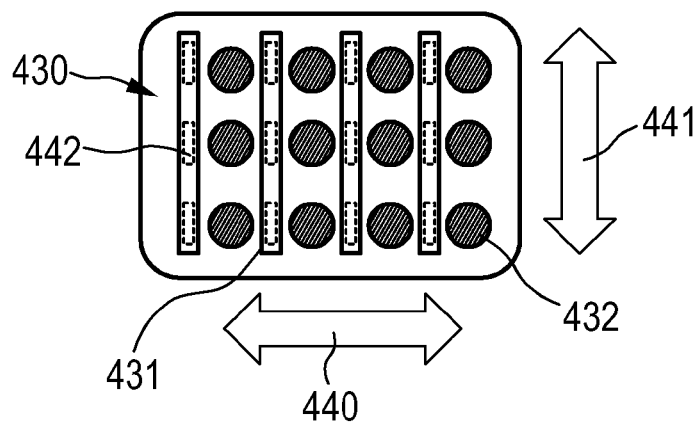

FIG. 12 shows schematically and exemplarily a further embodiment of a sensing surface 430 which can also be used with the sensing device and the analyzing device described above.

The sensing surface 430 comprises several sensing sites 432 arranged in parallel lines, wherein between the parallel lines reference sites 431 are located. The reference sites 431 have an elongated shape with a longitudinal and a transversal dimension. The longitudinal dimension is parallel to the parallel lines of the sensing sites 432. The length of the longitudinal dimension of the reference sites 431 is substantially equal to the length of the parallel lines of the sensing sites 432. The reference sites 431 are arranged in parallel lines interleaved with the parallel lines formed by the sensing sites 432. The longitudinal dimension of the reference sites 431 extends in a deformation direction 441 in which the sensing surface 430 is more deformable than in another direction 440. In this embodiment, the deformation direction 441 is the direction of strongest deformations and the direction 440 is the direction of weakest deformations.

In this embodiment, the normalization unit 34 is preferentially adapted to use reference signals for normalization which correspond to reference regions 442 within the reference sites 431, which can be defined by projections of the nearest sensing sites 432 onto the respective reference site 431 in a direction being orthogonal to the direction of the strongest deformations 441. The reference regions 442 can be defined as projections of the nearest sensing sites 432 in the horizontal direction in FIG. 12.

The reference signals of the nearest reference regions 442 are preferentially combined and the combined reference signal is preferentially used for normalizing the respective sensing signal. Also this combination is preferentially an average of the reference signals of the reference regions being the nearest neighbor reference regions to the respective sensing site, and also this averaging is preferentially performed in accordance with equation (1).

Figure 13:
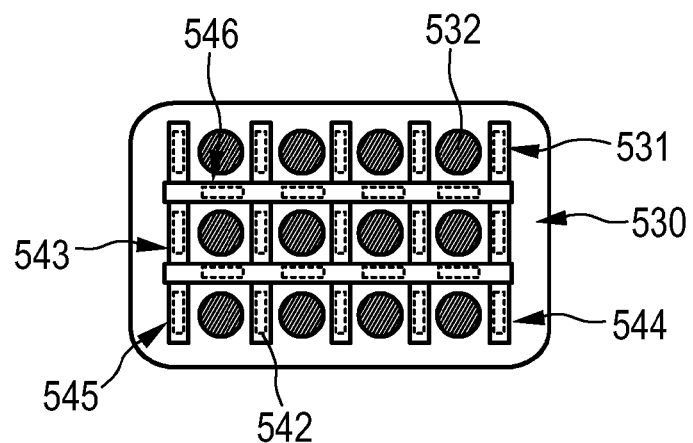

FIG. 13 shows schematically and exemplarily a further embodiment of a sensing surface 530 which can also be used by the above described sensing device and analyzing device.

The sensing surface 530 comprises several reference sites forming a grid 531 with several grid elements 543 being meshes. Several sensing sites 532 are arranged within the meshes 543. The grid 531 is formed by a first group 546 of parallel elongated reference sites, which is arranged on top of a second group 545 of parallel elongated reference sites being orthogonal to the parallel elongated reference sites of the first group 546.

For normalizing a sensing signal preferentially reference signals are used which correspond to reference regions 542 within the parallel elongated reference sites. The reference regions 542 can be defined by projections of the respective nearest sensing site 532 onto the respective elongated reference site in a direction orthogonal to the extension of the respective elongated reference site. For normalizing a sensing signal of a sensing site 532 reference signals of the nearest reference regions 542 are preferentially combined, in particular, in vertical and in horizontal direction, and the resulting combined reference signal is preferentially used for normalizing the respective sensing signal. Also in this embodiment, this combination of the reference signals of the nearest reference sites is preferentially an averaging, in particular, in accordance with equation (1).

Figure 14:
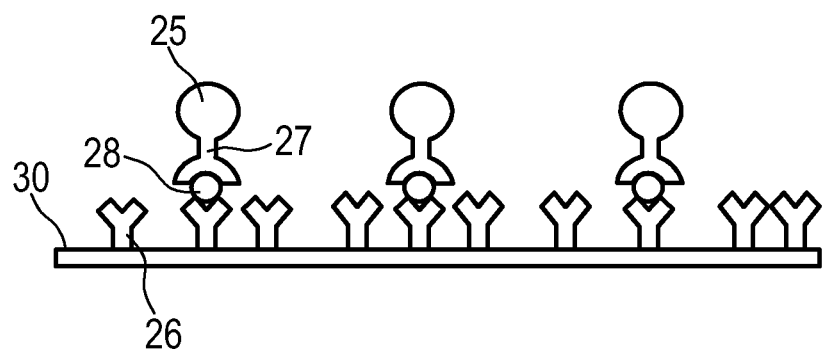
FIG. 14 shows schematically and exemplarily a sensing site at which magnetic beads which have attached a substance within a fluid are bound to a sensing site of a sensing surface.

FIG. 14 shows schematically and exemplarily a sensing site in more detail. The sensing site is preferentially adapted to allow sensing a substance within a fluid being, for example, a target molecule or a larger object in the fluid. In this embodiment, this is realized by a so-called sandwich essay. Magnetic beads 25 are coated with a specific antibody 27 that attaches to a target molecule 28 present in the fluid. When the magnetic beads that are freely present in the fluid have reacted with the available target molecules, the beads are attracted to the sensing surface 30 that has been coated with another antibody 26 that can couple to a target molecule. After a sufficiently long reaction time the magnetic field is switched such that the unbound magnetic beads are pulled upwards so that only the specifically bound beads with the correct target molecules stay attached to the surface. At that moment the detector 23 can be read out and gives a sensing signal that carries the information on the amount of target molecules in the fluid. So the sensing site is preferentially covered with a bio layer with antibodies.

The reference site is preferentially a site being adapted such that the corresponding reference signal is not influenced by the fluid, the substance within the fluid or magnetic beads. In the above described embodiments, the reference site is a TWR.

As explained above, the sensing surface of the sensing device can comprise several sensing sites and several reference sites. Referring again to FIG. 4, the analyzing device 18 can be operated in a calibration mode and in a measurement mode. The analyzing device 18 comprises a determination unit 46 for determining in the calibration mode for a sensing site of the several sensing sites at least one reference site of the several reference sites for normalization such that a drift variation of the normalized sensing signal is within a noise variation of the normalized sensing signal. The analyzing device 18 is adapted to normalize, in the measurement mode, the sensing signal of the sensing site of the several sensing sites by the at least one reference signal of the at least one reference site determined by the determination unit 46. This allows adapting the normalization process to the actually present spatially non-uniform fluctuations which are not caused by spatially non-uniform fluctuations of the substance at the sensing sites, thereby decreasing the influence of the spatially non-uniform fluctuations on the normalized sensing signal. The calibration in the calibration mode is preferentially performed for each sensing site.

In a further embodiment, it is not distinguished between a calibration mode and a measurement mode. Reference signals and sensor signals are being retrieved at the same time, for example, in the same CCD frame, and based on the retrieved reference and sensor signals for each sensing site of several sensing sites at least one reference site of the several reference sites is determined for normalizing such that a drift variation of the normalized sensing signal of the sensing site of the several sensing sites is within a noise variation of the normalized sensing signal of the sensing site of the several sensing sites. For this determination of the at least one reference site, which is used for normalizing the respective sensing signal, the normalized sensing signal is determined, wherein this already determined normalized sensing signal does not have to be determined again. Thus, in this embodiment, there is no need to switch between a calibration mode and a measurement mode.

The analyzing device 18 further comprises a concentration value generating unit 47 for generating a concentration value of the target substance within the fluid depending on the normalized sensing signal of the respective sensing site. Preferentially, the concentration value generating unit 47 comprises a storing unit in which assignments between normalized sensing signals and concentrations of the target substance are stored. These assignments are preferentially determined by calibration measurements, wherein normalized sensing signals are measured, when a known concentration of the target substance is present at the respective sensing site.

The analyzing device 18 further comprises an output unit 48 for outputting the generated concentration value. The output unit 48 is preferentially a display. The analyzing device 18 further comprises a control unit 49 for controlling the signal generating unit 33, the magnetic element 19, the normalization unit 34, the determination unit 46, the concentration value generating unit 47 and the output unit 48.

The sensing device 1 is a cartridge for receiving a fluid like blood, saliva or urine, for filtering the fluid and for transferring the filtered fluid to the sensing sites of the cartridge. The cartridge is disposable and is adapted for single use only. The analyzing device 18 is adapted to be used several times with different cartridges. Thus, a fluid 3 like blood, saliva or urine is put on the filter element 2 of the sensing device 1, the fluid 3 is filtered and the filtered fluid is transferred to the sensing location 7 in which the sensing site is present. The sensing device 1, i.e. in this embodiment the cartridge, is arranged in the analyzing device 18 and a substance within the fluid 3 at the sensing location, in particular, at the sensing site, is analyzed by the analyzing device 18. After the sensing device 1 has been used, it is preferentially discarded, whereas the analyzing device 18 is used for a next analyzing procedure.

The analyzing device 18 further comprises an aligning unit 50 for detecting the position of the one or several reference sites of the sensing device and for aligning the sensing device 1 and the analyzing device 18 with respect to each other by using the detected position of the one or several reference sites. The aligning unit 50 is adapted to detect the position of the one or several reference sites based on the reflected light detected by the detector 23. Preferentially, the detector 23 is a camera like a CCD camera, wherein the camera generates a two-dimensional image of the illuminated sensing surface. In this image the position of the one or several reference sites can be determined by determining regions within the image having a reflected intensity being larger than a threshold value. If the determined position of the one or several reference sites in this image correspond to stored positions which are preferentially determined by calibration and which indicate a correct alignment, the aligning unit 50 determines that the sensing device 1 and the analyzing device 18 are correctly aligned with respect to each other. If this is not the case, the output unit 48 outputs preferentially a signal to a user like a corresponding information on a display or like an acoustical signal. Also the aligning unit 50 is controlled by the control unit 49.

The sensing device 1 and the analyzing device 18 form a sensing system for sensing a substance in a fluid.

Figure 15:
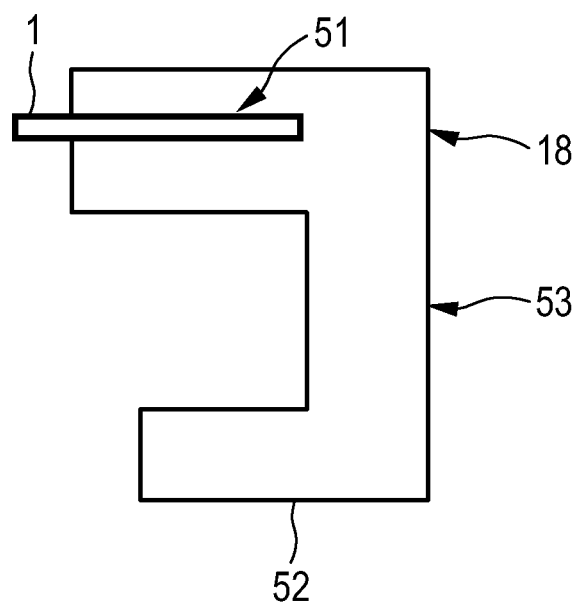
FIG. 15 shows schematically and exemplarily a sensing device introduced into an analyzing device.

The several units of the analyzing device 18 are preferentially arranged within a casing 52, which is schematically and exemplarily shown in FIG. 15 and which can comprise a grip part 53 for allowing a user to hold the analyzing device 18 in the hand while analyzing the substance in the fluid. The casing 52 comprises a receiving section 51 for receiving the sensing device 1. In other embodiments, the casing 52 can have another shape.

Figure 16:
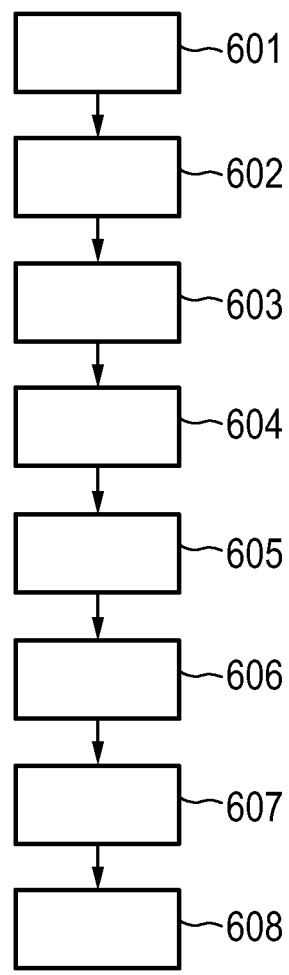
FIG. 16 shows a flowchart exemplarily illustrating a sensing method for sensing a substance in a fluid.
Figure 17:
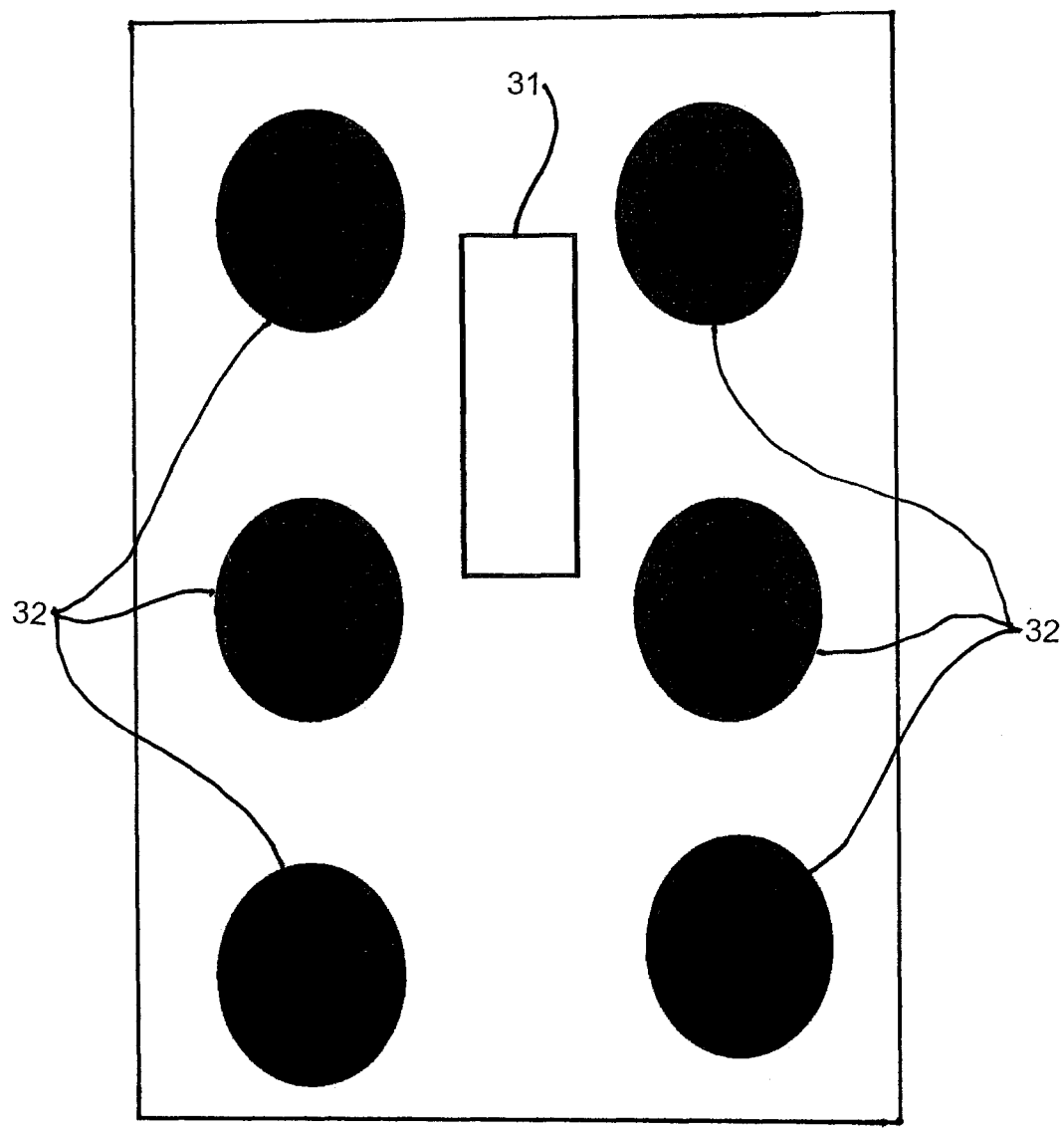
FIG. 17 shows schematically and exemplarily a sensing surface comprising a single reference site and a plurality of sensing sites.

In the following a sensing method for sensing a substance in a fluid will exemplarily be described with reference to a flowchart shown in FIG. 16.

In step 601, a fluid sample, in particular, a blood sample, is arranged on the filter element 2.

In step 602, the fluid is filtered by the filter element 2, and in step 603 the filtered fluid is transferred to the sensing location by capillary forces generated by the connecting channel and the guiding channels of the capillary structure.

Before, while or after performing steps 601 to 603 the sensing device 1 has been introduced into the analyzing device 18. At the sensing location 7 magnetic beads coated with a specific antibody that attaches to a target molecule present in the fluid are located. They mix with the filtered fluid, and the magnetic beads with the specific antibody attached to the target molecules within the fluid in step 604.

In step 605, the magnetic element 19 is controlled such that the magnetic beads at the sensing location are forced onto the sensing surface at which the one or several sensing sites are located. The magnetic beads with the attached target molecules bind to the one or several sensing sites on the sensing surface and in step 606 the magnetic element 19 is controlled such that magnetic forces pull the magnetic beads, which have not bound to one or several sensing sites, away from the one or several sensing sites so that only the specifically bound magnetic beads with the correct target molecules stay attached to one or several sensing sites.

In step 607, a sensing signal is generated by sensing the substance, i.e. the magnetic beads, at a sensing site and a reference signal is generated by sensing a reference site. In step 608, a normalized sensing signal is generated by normalizing the sensing signal using the reference signal. If several sensing sites leading to several sensing signals are present, each sensing signal is preferentially normalized. If several reference sites leading to several reference signals are present, preferentially several reference signals are combined to a combined reference signal, wherein the combined reference signal is used for normalizing a sensing signal. The combined reference signal is preferentially different for normalizing different sensing signals. The generated one or several sensing signals and the generated one or several reference signals correspond to one or several sensing sites and one or several reference sites which are arranged such that a drift variation of the normalized sensing signal is within a noise variation of the normalized sensing signal.

The normalization suppresses low spatial frequencies, i.e. substantially common mode disturbances. The normalization acts therefore as a spatial high-pass filter, wherein the cut-off frequency is determined by the arrangement of one or several sensing sites and one or several reference sites on the sensing surface, in particular, the cut-off frequency is determined by the distances between the one or several sensing sites and the one or several reference sites.

In the prior art in a low concentration regime, i.e. a concentration of the substance within the fluid below 10 pM, the instability of the normalized intensity amplitude exceeds the desired sensing signal originating from the respective sensing site. The invention is based on the recognition that the sensing device comprises strong non-uniform deformations. In particular, if the sensing device is a plastic cartridge being clamped, the mechanical stiffness of the plastic cartridge in combination with non-uniformities in its clamping mechanism introduces strong non-uniform deformations in the cartridge which change the reflected light from each sensing site differently, if light is directed to the sensing sites for sensing the substance in the fluid by using FTIR. This results, in the prior art, to a poor correlation of the reference signal with the sensing signal at the several sensing sites. Moreover, the cartridge is generally non-uniformly illuminated because of spatial and temporal fluctuations of the non-uniform intensity distribution of the emitting light source. Also this changes the amount of light reflected from each position of the sensing surface. These effects are further pronounced by cartridge translation/deformation and non-uniform bindings. Furthermore, all of these effects are strongly temperature dependent.

Thus, in the prior art fluctuations of the normalized sensing signal are present, which are not caused by fluctuations of the substance on the sensing sites and which might be due to (i) changing cartridge geometry, (ii) changing cartridge material properties such as refractive index and birefringence, (iii) changing intensities due to external disturbances in the light path, such as dust or water condensation, (iv) changing illumination profile due to temperature variations of the emitting light source.

These fluctuations of the normalized sensing signal in the prior art can be regarded as high frequency disturbances, i.e. disturbances having a spatial frequency being larger than the cut-off frequency of the normalization process of the prior art. The prior art normalization process does therefore not suppress these high frequency disturbances.

The invention is based on the recognition that the cut-off frequency of the normalization process can be increased by arranging the one or several sensing sites and the one or several reference sites accordingly. Thus, the invention is based on the recognition that the cut-off frequency of the normalization process can be modified by changing the arrangement of the one or several sensing sites and of the one or several reference sites.

The dimensions and the mutual distances of reference sites and sensing sites can be non-uniform distributed across the sensing surface as a result of an optimization towards maximum stability versus maximum binding area for a given cartridge/assay system.

Prior the actual assay measurement circle an optimum set of available TWR regions, i.e. sensing sites, can be identified for each binding spot, i.e. each sensing site, during a calibration measurement in the calibration mode, thereby guaranteeing a maximum correlation between the non-uniform sensing signal fluctuations with the actual sensing signal obtained from the binding spots during the assay measurement circle.

Preferentially, a sensing signal of a sensing site is normalized by using at least one reference signal of at least one reference site, wherein the distance between the sensing site and the respective at least one reference site is less than 100 µm. This pushes the effective spatial cut-off frequency of the normalization process upwards to higher frequencies, away from the high-frequency disturbances. This effective suppression is preferentially optimized by locating and/or selecting reference sites, in particular, TWRs, or areas inside the reference sites, in particular, inside the TWRs, in the direction of the weakest deformations, hence orthogonal to the strongest deformations. For further increasing the cut-off frequency of the normalization process reference signals of several reference sites may be weighted before being used for normalizing a sensing signal.

The sensing signal variations are preferentially considered as multiplicative gain variations.

Smaller sensing sites and reference sites at shorter distance increase the obtainable stability, but decrease the effective binding surface area, thereby increasing the shot noise, i.e. the photon- and binding-counting statistics of the actual sensing signal. The embodiments described above with reference to FIGS. 6, 10 to 13 provide a good balance between spot-dimensions, i.e. counting noise and system noise, and stability.

The shape of the reference site and the shape of the sensing site can be a circle or another shape like a rectangular shape.

If the reference site and the sensing site are integrated as described above with reference to FIG. 10, a dedicated area in or adjacent to a sensing site can preferentially not bind magnetic beads, which have attached the target substance, for defining a reference site integrated into a sensing site.

In the calibration mode, preferentially for each of the sensing sites reference sites are determined by the determination unit which optimize the normalization process in a way that the fluctuations of the normalized sensing signal, which are not caused by fluctuations of the substance at the sensing sites, are decreased.

Although in the above described embodiment the aligning unit is adapted to detect the position of one or several reference sites of the sensing device and to align the sensing device and the analyzing device with respect to each other by using the detected position of the one or several reference sites, in addition or alternatively alignment markers present on the sensing device can be used for the alignment procedure, in particular, for aligning the cartridge with respect to a camera frame of the analyzing device.

In the above described embodiment, the fluid was preferentially blood. In other embodiments, the fluid can be any other fluid, in particular, any other body fluid, like saliva or urine. The preferred application for the sensing device and for the analyzing device is in the field of point-of-care diagnostics, in particular, based on a finger prick blood sample, like a cardiac marker detection application. But, the sensing device can also be adapted for sensing other fluids, like saliva for Drugs Of Abuse.

In the above described embodiment, the analyzing device apparatus uses evanescent field techniques for determining the amount of magnetic beads on the surface. In other embodiments, other techniques can be used for determining these beads. For example, magnetic methods, sonic detection, electrical detection and combinations therefore can be used. Furthermore, the analyzing device can comprise any sensor based on the detection of the magnetic properties of the beads on or near to a sensor surface. The analyzing device can be adapted for detecting molecular targets, which often determine the concentration and/or presence of larger moieties, for example, cells, viruses, fractions of cells or fractions of viruses, tissue extract et cetera. The magnetic beads can be detected directly by the sensing method. As well, the particles can be further processed prior to detection, an example of further processing is that materials are added or that the chemical, biochemical or physical properties of the magnetic labels are modified to facilitate detection. The analyzing device can be adapted for working together with several biochemical assay types, for example, binding/unbinding assay, sandwich assay, competition assay, displacement assay, enzymatic assay et cetera. The sensing device and the analyzing device can be adapted for sensor multiplexing, i.e. the parallel use of different sensors and sensor surfaces, label multiplexing, i.e. the parallel use of different types of labels, and chamber multiplexing, i.e. the parallel use of different reaction chambers. The sensing device and the analyzing device can be used as rapid, robust and easy to use point-of-care biosensors for small sample volumes. The sensing cavity is preferentially a part of a disposable cartridge, which is to be used with the analyzing device, which contains one or more magnetic field generating means, i.e. the magnetic element, and one or more detection means. The sensing device and the analyzing device can preferentially be adapted for a use in automated high-throughput testing.

The magnetic beads are preferentially nano-particles having at least one dimension ranging between 3 nm and 5000 nm, preferably between 10 nm and 3000 nm, more preferred between 50 nm and 1000 nm.

Although in the above described embodiments a certain sensing device and a certain analyzing device have been described, in other embodiments, the sensing device and the analyzing device can have another structure. For example, the sensing device can just comprise a sensing surface with sensing sites and reference sites. Or another kind of filter can be used or another channel structure can be used for transferring filtered fluid from a filter location to a sensing location.

Although in the above described embodiment the sensing system is comprised of a sensing device and an analyzing device, in another embodiment the sensing system can be an integrated system comprising at least a sensing site, a reference site, a signal generation unit and a normalization unit, wherein the sensing site, the reference site, the signal generation unit and the normalization unit are not distributed over several separate devices.

Although in the above described embodiments several distributions of reference and sensing sites have been described, also other distributions of sensing and reference sites are possible. For example, only one of the different kinds of combined sensing and reference sites described above with reference to FIG. 10 can be used in a sensing system. Moreover, the combined reference and sensing sites shown in FIG. 10 can be combined with the distributions shown in FIGS. 6, 11 to 13.

Although in an above described embodiment a combination of reference signals of reference sites being nearest neighbors to a sensing site has been described as being used for normalizing the sensing signal of the respective sensing site, also second nearest neighbors or neighbors which are more far away can be combined for normalizing the sensing signal of the respective sensing site.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

Functions like the determination of reference signals for normalizing a sensing signal, generating a concentration value or normalizing a sensing value, performed by one or several units or devices can be performed by any other number of units or devices. The functions like the above mentioned functions and/or the control of the sensing system, in particular, of the analyzing device, in accordance with the above described sensing method can be implemented as program code means of a computer program and/or a dedicated hardware.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention relates to a sensing system for sensing a substance in a fluid. The sensing system comprises a sensing site at which the substance is to be sensed and a reference site. A signal generation unit generates a sensing signal by sensing the sensing site and a reference signal by sensing the reference site. The reference signal is used for normalizing the sensing signal, wherein the sensing site and the reference site are arranged such that a drift variation of the normalized sensing signal is within a noise variation of the normalized sensing signal. This improves the accuracy of the normalized sensing signal.

The invention claimed is:

1. A sensing system for sensing a substance in a fluid, the sensing system comprising:
a sensing site at which the substance is to be sensed,
a reference site,
a signal generation unit for generating a sensing signal by sensing the sensing site and for generating a reference signal by sensing the reference site,
a normalization unit for generating a normalized sensing signal by normalizing the sensing signal using the reference signal,
wherein the reference site and the signal generation unit are adapted such that the reference signal is not influenced by the substance and the fluid and the sensing site and the signal generation unit are adapted such that the sensing signal is dependent on the substance at the sensing site,
wherein the sensing site and the reference site are arranged such that a drift variation of the normalized sensing signal is within a noise variation of the normalized sensing signal,
wherein the sensing site and the reference site are integrated, the integrated sensing and reference site including a central sensing region with a radial reference region, the central sensing region partially covering the radial reference region.

2. The sensing system as defined in claim 1, wherein a distance between the sensing site and the reference site is smaller than 100 μm.

3. The sensing system as defined in claim 1, wherein the sensing system comprises a plurality of sensing sites and a plurality of reference sites, wherein the sensing system is adapted to be operated in a calibration mode and in a measurement mode, wherein the sensing system comprises a determination unit for determining, in the calibration mode, one sensing site of the plurality of sensing sites and at least one reference site of the plurality of references sites for normalizing such that a drift variation of the normalized sensing signal of the sensing site is within a noise variation of the normalized sensing signal, wherein the sensing system is adapted to normalize, in the measurement mode, the sensing signal of the sensing site by the at least one reference signal of the at least one reference site determined by the determination unit.

4. The sensing system as defined in claim 1, wherein the sensing system comprises a plurality of sensing sites and a plurality of reference sites, wherein the plurality of sensing sites and the plurality of reference sites are arranged in alternating parallel lines, each alternating parallel line including a plurality of either sensing or reference sites.

5. The sensing system as defined in claim 4, wherein the plurality of sensing sites and the plurality of reference sites are arranged in an interleaved manner.

6. The sensing system as defined in claim 4, wherein the plurality of sensing sites and the plurality of reference sites are arranged such that at least one sensing site of the plurality of sensing sites has a plurality of reference sites as nearest neighbors in at least two directions.

7. The sensing system as defined in claim 4, wherein the sensing system comprises a plurality of sensing sites collinearly aligned with a deformation direction.

8. The sensing system as defined in claim 1, wherein the sensing system comprises a plurality of reference sites forming a grid with a plurality of grid elements and a plurality of sensing sites, wherein the plurality of sensing sites are arranged within the plurality of grid elements, the grid formed by a first group of parallel elongated reference sites and a second group of parallel elongated reference sites orthogonal to first group of parallel elongated reference sites.

9. The sensing system as defined in claim 1, wherein the sensing system comprises a sensing device including the sensing site and the reference site and an analyzing device including the signal generation unit and the normalization unit, wherein the analyzing device further comprises an aligning unit for detecting the position of the reference site of the sensing device and for aligning the sensing device and the analyzing device with respect to each other by using the detected position of the reference site.

10. A sensing system for sensing a substance in a fluid, the sensing system comprising:
   a plurality of sensing sites configured to receive the substance is to be sensed, the plurality of sensing sites collinearly aligned with a deformation direction which is orthogonal to another direction, the sensing system being more deformable in one of the deformation direction and the another direction than in the other,
   a reference site,
   a signal generation unit configured to generate a sensing signal by sensing the sensing site and for generating a reference signal by sensing the reference site,
   a normalization unit configured to generate a normalized sensing signal by normalizing the sensing signal using the reference signal,
   wherein the reference site and the signal generation unit are configured such that the reference signal is not influenced by the substance and the fluid and the sensing site and the signal generation unit are configured such that the sensing signal is dependent on the substance at the sensing site,
   wherein the sensing site and the reference site are arranged such that a drift variation of the normalized sensing signal is within a noise variation of the normalized sensing signal.

11. A sensing device for cooperating with an analyzing device which clamps the sensing device in an analysis position, a mechanical stiffness of the sensing device and non-uniformities in the clamping causing deformations in the sensing device which result in drift variations in signals in the analyzing device, the sensing device comprising:
   a substrate having a deformation direction normal to the axis along which the substrate deforms in which the substrate is more deformable than in a direction transverse to the deformation direction;
   a plurality of sensing sites carried by the substrate and configured to receive samples of a fluid to be analyzed, the plurality of sensing sites being disposed in rows aligned with the deformation direction; and
   a plurality of reference sites carried by the substrate and configured to receive reference samples, the reference sites being disposed in rows aligned with the deformation direction and interleaved with the rows of sensing sites.

12. A sensing device for sensing a substance in a fluid, comprising:
   a plurality of sensing sites at which the substance is to be sensed,
   a reference site consisting of a single reference site,
   wherein the plurality of sensing sites are arranged in parallel lines and the reference site is arranged between the plurality of sensing sites, the reference site having an elongated shape with a longitudinal and transversal direction, wherein the longitudinal dimension is parallel to the parallel lines of the sensing sites.

13. A sensing system for sensing a substance in a fluid, the sensing system comprising:
   a plurality of sensing sites at which the substance is to be sensed, the plurality of sensing sites arranged in parallel lines,
   a reference site, consisting of a single reference site, having an elongated shape and being disposed between the parallel lines of the sensing sites,
   a signal generation unit for generating sensing signals by sensing the sensing sites and for generating a reference signal by sensing the reference site,
   a normalization unit for generating normalized sensing signals by normalizing the sensing signals using the reference signal,
   wherein the reference site and the signal generation unit are adapted such that the reference signal is not influenced by the substance and the fluid and the sensing sites and the signal generation unit are adapted such that the sensing signals is dependent on the substance at the sensing sites,
   wherein the sensing site and the reference site are arranged such that a drift variation of the normalized sensing signals is within a noise variation of the normalized sensing signals.

14. The sensing system as defined in claim 13, wherein the elongated shape has a longitudinal and a transversal dimension, wherein the longitudinal dimension is parallel to the parallel lines of the sensing sites.

* * * * *